US010827989B2

(12) United States Patent
Vancamberg et al.

(10) Patent No.: US 10,827,989 B2
(45) Date of Patent: Nov. 10, 2020

(54) SYSTEM AND METHOD FOR IMAGING BIOPSY SAMPLES OBTAINED FROM A PATIENT

(71) Applicant: GENERAL ELECTRIC COMPANY, Schenectady, NY (US)

(72) Inventors: Laurence Vancamberg, Poissy (FR); Razvan Iordache, Paris (FR); Pierre Tudal, Guyancourt (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 598 days.

(21) Appl. No.: 15/385,046

(22) Filed: Dec. 20, 2016

(65) Prior Publication Data

US 2018/0168523 A1   Jun. 21, 2018

(51) Int. Cl.
*A61B 6/00* (2006.01)
*A61B 6/06* (2006.01)
*A61B 10/02* (2006.01)
*A61B 6/04* (2006.01)

(52) U.S. Cl.
CPC .............. *A61B 6/06* (2013.01); *A61B 6/0414* (2013.01); *A61B 6/40* (2013.01); *A61B 6/461* (2013.01); *A61B 6/502* (2013.01); *A61B 10/0233* (2013.01)

(58) Field of Classification Search
CPC ........... A61B 6/0414; A61B 6/06; A61B 6/40; A61B 6/461; A61B 6/502; A61B 10/0233
See application file for complete search history.

(56) References Cited

U.S. PATENT DOCUMENTS

| 5,660,185 A | 8/1997 | Shmulewitz et al. |
| 7,715,523 B2 | 5/2010 | Lafferty |
| (Continued) | | |

FOREIGN PATENT DOCUMENTS

| EP | 2 772 191 A1 | 9/2014 | |
| EP | 2772191 | * 9/2014 | ............... A61B 6/00 |
| (Continued) | | | |

OTHER PUBLICATIONS

English translation of JP 2015085056 (Year: 2015).*
(Continued)

*Primary Examiner* — Eric D. Bertram
(74) *Attorney, Agent, or Firm* — Grogan, Tuccillo & Vanderleeden, LLP

(57) ABSTRACT

A system for imaging biopsy samples obtained from a patient includes: a radiation source; a radiation detector having a surface that defines a first imaging region, a second imaging region, and a third imaging region; and a collimator having a body defining an opening and selectively adjustable between a first imaging position and a second imaging position. The first imaging position allows radiation rays to pass from the radiation source, through the opening, and into the second imaging region while restricting the radiation rays from passing into the first imaging region when the radiation source is in a first scanning position. The second imaging position allows radiation rays to pass from the radiation source, through the opening, and into the third imaging region while restricting the radiation rays from passing into the first imaging region when the radiation source is in a second scanning position.

9 Claims, 4 Drawing Sheets

(56) References Cited

U.S. PATENT DOCUMENTS

| | | | | |
|---|---|---|---|---|
| 7,826,588 B2 * | 11/2010 | Eliasson | ................ | A61B 6/502 |
| | | | | 378/37 |
| 2009/0225935 A1 * | 9/2009 | Eliasson | ................ | A61B 6/502 |
| | | | | 378/37 |
| 2011/0021947 A1 * | 1/2011 | Nakayama | ........... | A61B 6/0414 |
| | | | | 600/567 |
| 2014/0241500 A1 * | 8/2014 | Yasuda | ................... | A61B 6/06 |
| | | | | 378/62 |
| 2017/0082557 A1 * | 3/2017 | Iordache | ................ | A61B 6/025 |

FOREIGN PATENT DOCUMENTS

| | | | | |
|---|---|---|---|---|
| JP | 2015-085056 A | 5/2015 | | |
| JP | 2015085056 | * 7/2015 | ............... | A61B 6/00 |

OTHER PUBLICATIONS

Extended European Search Report and Opinion issued in connection with corresponding EP Application No. 17206631.8 dated May 17, 2018.

* cited by examiner

SYSTEM AND METHOD FOR IMAGING BIOPSY SAMPLES OBTAINED FROM A PATIENT

BACKGROUND

Technical Field

Embodiments of the invention relate generally to medial biopsy procedures, and more specifically, to a system and method for imaging biopsy samples obtained from a patient.

Discussion of Art

Many medical biopsy procedures concern obtaining a biopsy sample, i.e., a tissue sample, from a body part of a patient suspected as being cancerous, and then testing the biopsy sample for indications that the body part contains cancer cells. In many breast biopsy procedures, a needle is inserted into the breast manually or by using an automatic needle guidance system. In such procedures, the needle is typically guided to a suspect region within the breast via an x-ray imaging system which includes a ray source and a detector. The patient's breast is usually positioned on a breast support located between the detector and the ray source, and then held/compressed in place against the breast support by a compression plate. Compression of the breast in such a manner typically serves to stabilize the breast for improved x-ray imaging accuracy and guidance of the needle.

To improve the quality of the biopsy sample for the subsequent cancer tests, it is often desirable to verify that the biopsy sample contains micro-calcifications via x-ray imaging, and to obtain subsequent biopsy samples if needed. In order to limit the number of x-ray exposures to the patient, biopsy samples are often imaged by a second x-ray system different from the first x-ray system that was used to guide the needle to the suspect region. Many such second x-ray systems, however, are usually located in a different room than the first x-ray system. Thus, it typically takes a significant amount of time to remove the biopsy sample from the patient, transport the biopsy sample to the second x-ray system, and then image the biopsy sample with the second x-ray system. Moreover, the x-ray imaging data from the second x-ray system is usually stored separately from the x-ray imaging data from the first x-ray system. In other words, using two separate x-ray systems distributes the x-ray imaging data from a single biopsy procedure over multiple data sets which are typically stored separately.

Additionally, it is also usually desirable to keep the patient's breast compressed such that it does not move between biopsy samples. Thus, many breast biopsy procedures maintain compression of the patient's breast throughout the entire biopsy procedure, to include the time it takes to image the biopsy samples with a second x-ray system to verify that they contain micro-calcifications. Compression of the breast via the compression plate, however, is usually painful for the patient.

What is needed, therefore, is an improved system and method for imaging biopsy samples obtained from a patient.

BRIEF DESCRIPTION

In an embodiment, a system for imaging biopsy samples obtained from a patient is provided. The system includes: a radiation source operative to emit radiation rays and selectively adjustable between a first scanning position and a second scanning position; a radiation detector operative to receive the radiation rays and having a surface that defines a first imaging region, a second imaging region, and a third imaging region; and a collimator having a body defining an opening and operative to be disposed adjacent to the radiation source such that the collimator is selectively adjustable between a first imaging position and a second imaging position. The first imaging position allows one or more of the radiation rays to pass from the radiation source, through the opening, and into the second imaging region while restricting the radiation rays via the body from passing into the first imaging region when the radiation source is in the first scanning position. The second imaging position allows one or more of the radiation rays to pass from the radiation source, through the opening, and into the third imaging region while restricting the radiation rays via the body from passing into the first imaging region when the radiation source is in the second scanning position.

In another embodiment, a method for imaging a biopsy sample obtained from a patient is provided. The method includes: imaging a body part of the patient disposed in a first imaging region via a radiation source arranged in a first scanning position, the first imaging region defined by a surface of a radiation detector that receives radiation rays emitted by the radiation source and further defines a second imaging region and a third imaging region; obtaining the biopsy sample from the body part; and imaging the biopsy sample in the second imaging region via the radiation source arranged in the first scanning position with a collimator disposed adjacent to the radiation source and arranged in a first imaging position such that an opening defined by a body of the collimator allows one or more of the radiation rays emitted by the radiation source to pass into the second imaging region while the body restricts the radiation rays from passing into the first imaging region. The collimator is selectively adjustable to a second imaging position that allows one or more of the radiation rays emitted by the radiation source to pass through the opening and into the third imaging region while restricting the radiation rays via the body from passing into the first imaging region when the radiation source is arranged in a second scanning position.

In yet another embodiment, a collimator for a system for imaging biopsy samples obtained from a patient is provided. The collimator includes a body that defines an opening and is operative to be disposed adjacent to a radiation source of the system. When the body is in a first imaging position and the radiation source is in a first scanning position, the opening allows radiation rays emitted by the radiation source to pass through and into a first imaging region defined by a surface of a radiation detector of the system while restricting the radiation rays from passing into a second imaging region defined by the surface of the radiation detector. When the body is in a second imaging position and the radiation source is in a second scanning position, the opening allows radiation rays emitted by the radiation source to pass through and into a third imaging region defined by the surface of the radiation detector while restricting the radiation rays from passing into the second imaging region.

DRAWINGS

The present invention will be better understood from reading the following description of non-limiting embodiments, with reference to the attached drawings, wherein below:

DETAILED DESCRIPTION

Figure 1:
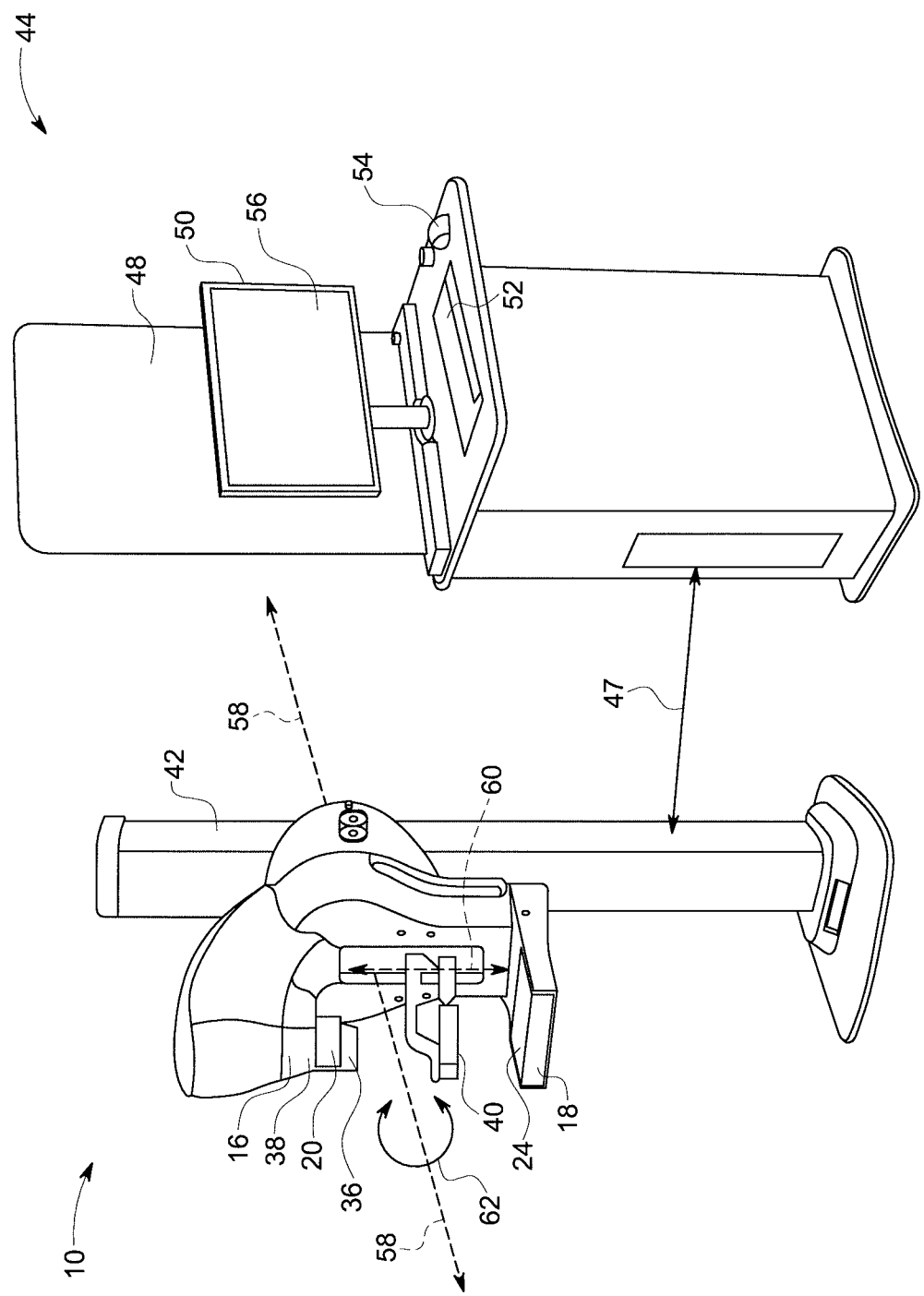
FIG. 1 is a perspective view of a system for imaging biopsy samples obtained from a patient, in accordance with an embodiment of the invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Further, while the embodiments disclosed herein are described with respect to a breast biopsy system and procedure, it is to be understood that embodiments of the present invention may be applicable to other types of biopsy procedures. Further still, as will be appreciated, embodiments of the present invention related imaging systems may be used to analyze tissue generally and are not limited to human tissue.

Figure 6:
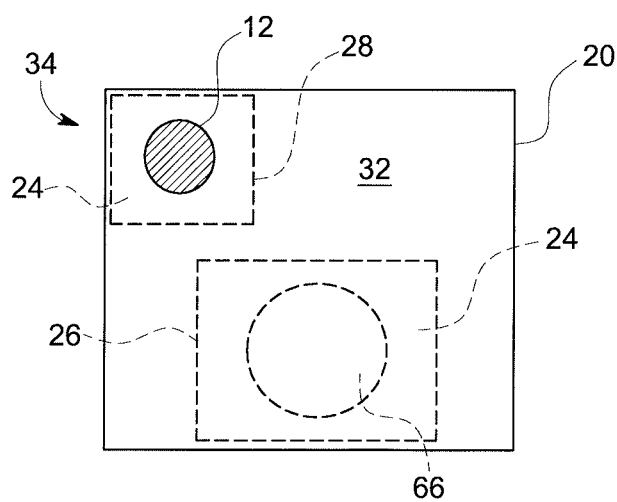
FIG. 6 is a diagram of the collimator of FIG. 3 overlaid on top of a radiation detector of the system of FIG. 1, in accordance with an embodiment of the invention.
Figure 7:
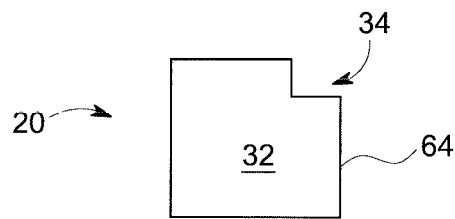
FIG. 7 is another top-down view of the collimator of the system of FIG. 3, wherein the collimator is in a second imaging position, in accordance with an embodiment of the invention.
Figure 8:
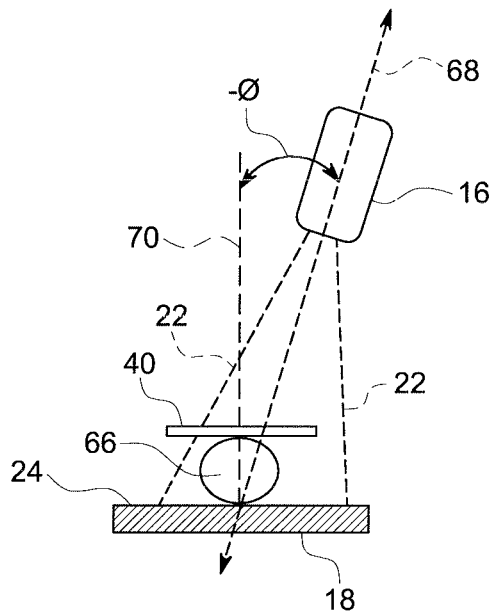
FIG. 8 is a diagram of the system of FIG. 4, wherein the radiation source is in a second scanning position, in accordance with an embodiment of the invention.
Figure 9:
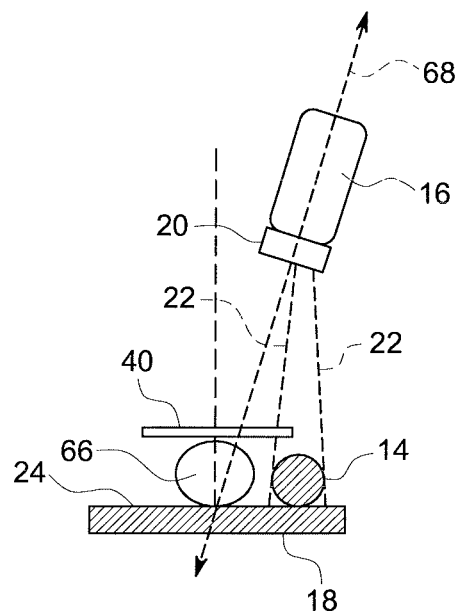
FIG. 9 is a diagram of the system of FIG. 8, wherein the radiation source is in the second scanning position and the collimator is in the second imaging position, in accordance with an embodiment of the invention.
Figure 10:
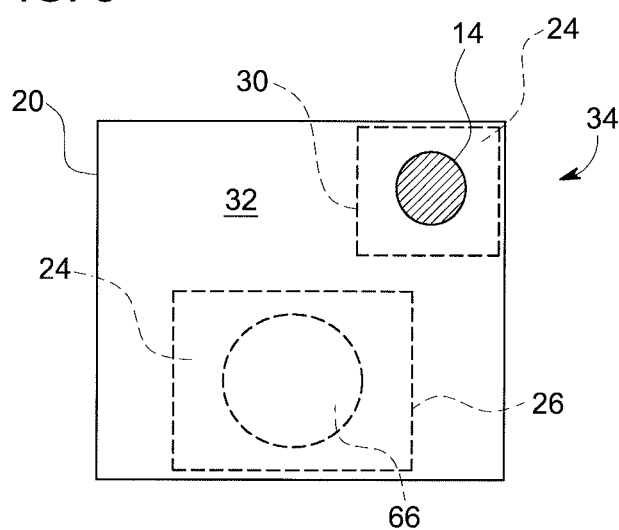
FIG. 10 is a diagram of the collimator of FIG. 7 overlaid on top of a radiation detector of the system of FIG. 1, in accordance with an embodiment of the invention.

Referring now to FIG. 1, the major components of a system 10 for imaging biopsy samples 12 and 14 (FIGS. 5, 6, 9, and 10) obtained from a patient incorporating an embodiment of the invention are shown. As will be appreciated, in embodiments, the biopsy samples 12, 14 may be stereotactic breast biopsies. The system 10 includes a radiation source/device 16, a radiation detector 18, and a collimator 20. The radiation source 16 is operative to emit radiation rays 22 (FIGS. 4, 5, 8, and 9) and is selectively adjustable between a first scanning position (FIGS. 4, and 5) and a second scanning position (FIGS. 8 and 9). The radiation detector 18 is operative to receive the radiation rays 22 and has a surface 24 that defines a first imaging region (depicted as the dashed box 26 in FIGS. 6 and 10), a second imaging region (depicted as the dashed box 28 in FIG. 6), and a third imaging region (depicted as the dashed box 30 in FIG. 10). The collimator 20 has a body 32 (best seen in FIGS. 3, 5, 6, 7, 9 and 10) that defines an opening 34 (FIGS. 3, 6, 7, and 10) and is operative to be disposed adjacent to the radiation source 16 such that the collimator 20 is selectively adjustable between a first imaging position (FIGS. 3, 5, and 6) and a second imaging position (FIGS. 7, 9, and 10). The first imaging position allows one or more of the radiation rays 22 to pass from the radiation source 16, through the opening 34, and into the second imaging region 28 while restricting the radiation rays, 22 via the body 32, from passing into the first imaging region 26 when the radiation source 16 is in the first scanning position. The second imaging position allows one or more of the radiation rays 22 to pass from the radiation source 16, through the opening 34, and into the third imaging region 30 while restricting the radiation rays 22, via the body 32, from passing into the first imaging region 26 when the radiation source 16 is in the second scanning position.

In embodiments, the system 10 may further include a patient shield 36 mounted to the radiation source 16 via face shield rails 38 for protecting the patient from the radiation rays 22, a compression plate 40, and a support structure 42 to which one or more of the radiation source 16, radiation detector 18, and/or compression plate 40 may be mounted to. In embodiments, the system 10 may further include a controller 44. In embodiments, the system 10 may further include a biopsy tool 46 (FIG. 2), e.g., a needle.

In embodiments, the controller 44 may be a workstation having at least one processor and a memory device as shown in FIG. 1 or, in other embodiments, the controller 44 may be embedded/integrated into one or more of the various components of the system 10 disclosed above. In embodiments, the controller 44 may be in electrical communication with the radiation source 16, radiation detector 18, the compression plate 40, and/or the biopsy tool 46 via a cable 47. As will be appreciated, in embodiments, the connection 47 may be a wireless connection. In embodiments, the controller 44 may include a radiation shield 48 that protects an operator of the system 10 from the radiation rays 22 emitted by the radiation source 16. The controller 44 may further include a display 50, a keyboard 52, mouse 54, and/or other appropriate user input devices, that facilitate control of the system 10 via a user interface 56.

As further shown in FIG. 1, the radiation source 16, along with the radiation detector 18, forms part of an x-ray system which provides x-ray imagery for the purpose of guiding the biopsy tool 46, e.g., needle, to a suspect site within a body part of a patient. As stated above, the radiation source 16 emits the radiation rays 22 such that the radiation rays 22 travel from the radiation source 16 to the radiation detector 18. While the radiation rays 22 are discussed herein as being x-rays, it is to be understood that the radiation source 16 may emit other types of electromagnetic rays which can be used to image a patient. The radiation source 16 may be mounted to the support structure 42 such that the radiation source can rotate around an axis 58 in relation to the radiation detector 18 and first imaging region 26.

As stated above, the radiation detector 18 receives the radiation rays 22 emitted by the radiation source 16. In embodiments, data regarding the radiation rays 22 received by the radiation detector 18 may be electrically communicated to the controller 44 from the radiation detector 18 via cable/electronic connection 47 such that the controller 44 generates one or more images which may be shown on the display 50.

The compression plate 40 is operative to move towards and away from the radiation detector 18 as indicated by arrows 60 such that the compression plate 40 holds a body part, e.g., a breast, in place against the surface 24 of the radiation detector 18.

Figure 2:
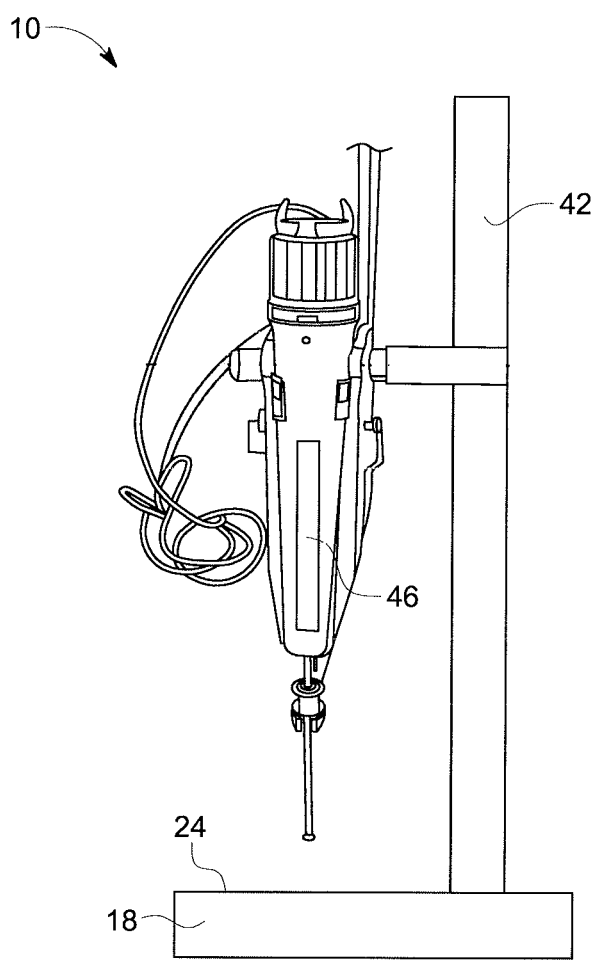
FIG. 2 is a perspective view of another embodiment of the system of FIG. 1 wherein the system includes a biopsy tool, in accordance with an embodiment of the invention.

As shown in FIG. 2, in embodiments, the biopsy tool 46, e.g., biopsy needle, may be disposed on the support structure 42 such that it also rotates about the axis 58, in a manner similar to the radiation source 16, and/or moves in a vertical and/or horizontal direction, in a manner similar to the compression plate 40.

Figure 3:
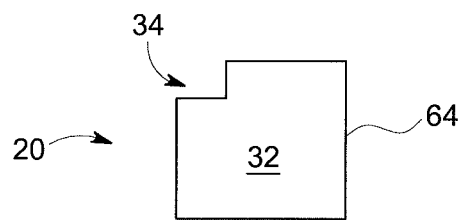
FIG. 3 is a top-down view of a collimator of the system of FIG. 1, wherein the collimator is in a first imaging position, in accordance with an embodiment of the invention.
Figure 4:
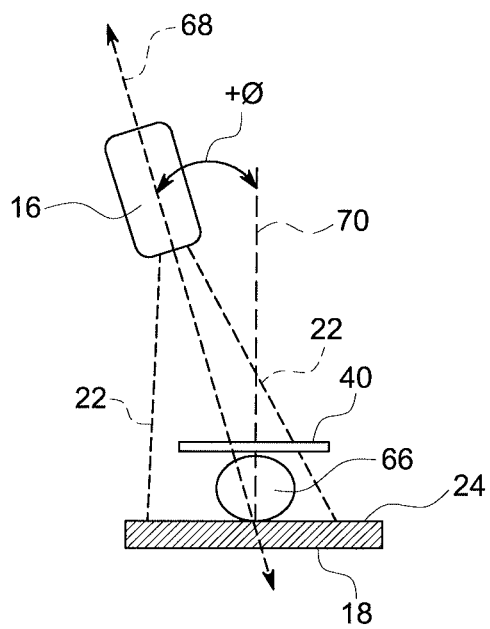
FIG. 4 is a diagram of the system of FIG. 1, wherein a radiation source of the system is in a first scanning position, in accordance with an embodiment of the invention.

Turning now to FIGS. 3 and 7, the body 32 of the collimator 20 is made of a substance that restricts the movement of radiation rays 22. For example, in embodiments, the body 32 may be made of lead. As stated above, the body 32 of the collimator 20 defines the opening 34. In embodiments, the opening 34 may be disposed along an outer edge 64 of the body 32. For example, in embodiments, the body 32 may have a rectangular shape and the opening 34 may be defined by a cut-away corner of the body 32 as shown in FIGS. 3 and 7. As used herein, the term cut-away corner means a shape resembling a rectangle that has had one of its corners removed, and/or folded back towards the center of the rectangle. As also stated above, the collimator 20 has a first imaging position (FIG. 3) and a second imaging position (FIG. 7).

The imaging positions of the collimator 20 are the positions/orientation of the body 32 in relation to the radiation detector 18, and in particular, to the end of the radiation detector 18 which emits the radiation rays 22. In embodiments, the collimator 20 may be attached to the radiation source 16 via the face shield rails 38 (FIG. 1). In other embodiments, the collimator 20 may slide in and out of a set of rails. In embodiments, when the collimator 20 is disposed adjacent to the radiation source 16 and in the first imaging position (FIG. 3), the opening 34 may be aligned with the second imaging region 28 (best seen in FIG. 6). Similarly, when the collimator 20 is disposed adjacent to the radiation source 16 and in the second imaging position (FIG. 7), the opening 34 may be aligned with the third imaging region 30 (best seen in FIG. 10). In embodiments, the body 32 may have a static shape. In other words, the shape of the body 32 does not substantially change between the first imaging position (FIG. 3) and the second imaging position (FIG. 6). For example, in embodiments, the collimator 20 may be selectively adjusted between the first and the second imaging positions by rotating and/or translating, i.e., an Euclidean translation, the body 32 in relation to the radiation source 16. Thus, as will be explained in greater detail below, the collimator 20 serves to control which regions of the radiation detector 18 receive the radiation rays 22 emitted via the radiation source 16.

Referring now to FIGS. 1, and 3-6, in operation in accordance with an embodiment, a body part 66 of the patient may be placed onto the surface 24 of the radiation detector 18 such that the body part 66 is within the first imaging region 26. The compression plate 40 then compresses the body part 66 against the surface 24 such that the body part 66 is immobilized. The radiation source 16 is then selectively adjusted such that it is moved/rotated to the first scanning position (FIG. 4) and scans the body part 66 in the first imaging region 26. The radiation detector 18 receives the radiation rays 22 passing through the body part 66 and sends data to the controller 44 which then generates one or more x-ray images of the body part 66. As will be appreciated, the orientation of the radiation source 16 in the first scanning position may be such that a longitudinal axis 68 of the radiation source 16 forms a positive angle $+\varnothing$ with a line 70 normal to the surface 24 of the radiation detector 18. The terms "positive" and "negative," as used herein with respect to the angle $\varnothing$ formed between the longitudinal axis 68 of the radiation source 16 and the line 70 normal to the surface 24 of the radiation detector 18, describe angles that are of opposite signs, i.e., a "positive" $\varnothing$ is an angle that has the opposite sign of a "negative" $\varnothing$.

Figure 5:
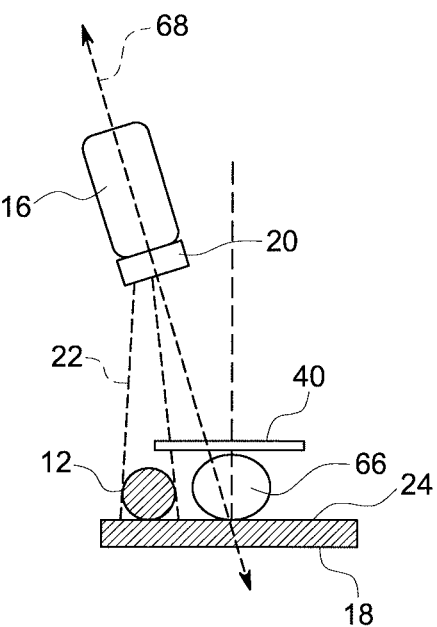
FIG. 5 is a diagram of the system of FIG. 4, wherein the radiation source is in the first scanning position and the collimator is in the first imaging position, in accordance with an embodiment of the invention.

A physician and/or the controller 44 then obtains one or more biopsy samples 12 using the x-ray imagery to guide the needle 46 to the suspect region within the body part 66. As shown in FIGS. 5 and 6, the biopsy samples 12 are then placed into the second imaging region 28 and the collimator 20 is then coupled to the radiation source 16 such that the collimator 20 is disposed adjacently to the radiation source 16. The collimator 20 is then selectively adjusted to be in the first imaging position so that the opening 34 aligns with the second imaging region 28. As will be appreciated, in embodiments, the collimator 20 may be integrated into the radiation source 16 such that the collimator 20 does not need to be coupled to the radiation source 16 for each biopsy sampling/imaging.

When the radiation source 16 is in the first scanning position and the collimator 20 is in the first imaging position, as shown in FIG. 5, the biopsy samples 12 are then imaged/scanned via the radiation source 16. Accordingly, the orientation of the collimator 20 in the first imaging position allows one or more of the radiation rays 22 to pass through the opening 34 and into the second imaging region 28 while restricting the radiation rays 22 from passing into the first imaging region 26. The radiation detector 18 then sends data concerning the received radiation rays 22 to the controller 44 which then generates imaging data, e.g., one or more images, of the biopsy samples 12. As will be appreciated, the imaging data of the biopsy samples 12 can then be accessed by a physician to determine if one or more of the biopsy sample 12 are sufficient for subsequent testing, e.g., the amount of micro-calcifications in one or more of the biopsy samples 12 is acceptable. If the physician determines that the biopsy samples 12 are insufficient, then one or more subsequent biopsy samples can be obtained without having to re-image the body part 66 in the first imaging region 26. The subsequent biopsy samples can then be imaged in the second imaging region 28 as described above.

Referring now to FIGS. 1 and 7-10, similar to the procedure of obtaining and imaging the biopsy samples 12 in the second imaging region 28, the system 10 may image one or more biopsy samples 14 in the third imaging region 30. For example, the radiation source 16 may be selectively adjusted such that it is rotated, translated, and/or otherwise moved to the second scanning position (FIG. 8). As will be appreciated, the orientation of the radiation source 16 in the second scanning position may be such that the longitudinal axis 68 of the radiation source 16 forms a negative angle $-\varnothing$ with the line 70 normal to the surface 24 of the radiation detector 18. Once in the second scanning position, the radiation source 16 scans the body part 66 in the first imaging region 26. As before, the radiation detector 18 receives the radiation rays 22 passing through the body part 66 and sends data to the controller 44 which then generates one or more x-ray images of the body part 66. The physician and/or the controller 44 then obtains the one or more biopsy samples 14 using the x-ray imagery to guide the biopsy tool 46 to the suspect region within the body part 66. As shown in FIGS. 9 and 10, the biopsy samples 14 are then placed into the third imaging region 30, and the collimator 20 is then coupled to the radiation source 16 such that it is disposed adjacently to the radiation source 16. The collimator 20 is then selectively adjusted to be in the second imaging position (FIGS. 7 and 10) such that the opening 34 aligns with the third imaging region 30.

When the radiation source 16 is in the second scanning position and the collimator 20 is in the second imaging position, as shown in FIG. 9, the one or more biopsy samples 14 are imaged/scanned via the radiation source 16. Accordingly, the orientation of the collimator 20 in the second imaging position allows one or more of the radiation rays 22 to pass through the opening 34 and into the third imaging region 30 while restricting the radiation rays 22 from passing into the first imaging region 26. The radiation detector 18 then sends data concerning the received radiation rays 22 to the controller 44 with then generates imaging data, e.g., one or more images of the biopsy samples 14. As will be appreciated, the imagery of the biopsy samples 14 can then be accessed by a physician to determine if the biopsy samples 14 are sufficient for subsequent testing, e.g., the amount of micro-calcifications in one or more of the biopsy samples 14 is acceptable. If the physician determines that the biopsy samples 14 are insufficient, then one or more subsequent biopsy samples can be obtained without having to re-image the body part 66 in the first imaging region 26. The subsequent biopsy samples can then be imaged in the third imaging region 30 as described above.

After the biopsy samples 12 and/or 14, and/or any subsequent biopsy samples, have been obtained and found to be acceptable, the compression plate 40 is moved away from the surface 24 of the radiation detector 18 such that the body part 66 is uncompressed.

Further, as will be appreciated, in embodiments, the system 10 may guide the biopsy tool 46 to obtain the one or more biopsy samples 12 or 14 based at least in part on two stereoscopic images of the suspect region in order to determine a set of three-dimensional ("3D") coordinates of the suspect region from which the biopsy samples 12 and/or 14 are obtained. As such, the collimator 20 may be selectively adjusted to either the first or the second imaging position based at least in part on whether Ø is positive or negative after the biopsy samples 12 or 14 have been obtained.

For example, the controller 44 may obtain a first and a second stereoscopic image of the suspect region via the radiation source 16 at the first and at the second scanning positions, respectively. The system 10 may then guide the biopsy tool 46 to obtain one or more biopsy samples 14 while the radiation source 16 is in the second scanning position. As the angle Ø formed by the longitudinal axis 68 of the radiation source 16 with the line 70 normal to the surface 24 of the radiation detector 18 is negative when the radiation source 16 is in the second scanning position, the biopsy samples 14 may be placed into the third imaging region 30 and the collimator 20 is selectively adjusted to the second imaging position so that the system 10 can image the biopsy samples 14 in the third imaging region 30 as described above.

Similarly, the controller 44 may obtain the first and the second stereoscopic image of the suspect region via the radiation source 16 at the second and at the first scanning positions, respectively. The system 10 may then guide the biopsy tool 46 to obtain one or more biopsy samples 12 while the radiation source 16 is in the first scanning position. As the angle Ø formed by the longitudinal axis 68 of the radiation source 16 with the line 70 normal to the surface 24 of the radiation detector 18 is positive when the radiation source 16 is in the first scanning position, the biopsy samples 12 may be placed into the second imaging region 28 and the collimator 20 is selectively adjusted to the first imaging position so that the system 10 can image the biopsy samples 12 in the second imaging region 28 as described above.

Accordingly, the physician/user of the system 10 may determine whether to image the biopsy samples 12, 14 in either the second imaging region 28 or the third imaging region 30 based at least in part on whether the radiation source 16 is at and/or near the first or the second scanning position, respectively, after having obtained one or more images used to guide the biopsy tool 46 to the suspect site.

As will be appreciated, the order of obtaining the two stereoscopic images of the suspect region, i.e., whether the first and the second stereoscopic images are obtained via the radiation source 16 at the first and at the second scanning positions, respectively, or vice versa, may be based at least in part on the initial position of the radiation source 16 at the start of the scanning procedure, user preference, and/or environmental factors. Further, in embodiments, the system 10 may guide the biopsy tool 46 to obtain the one or more biopsy samples 12 or 14 based at least in part on more than two images, i.e., tomosynthesis.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

Further, in embodiments, the system 10 may include a first collimator that directs the radiation rays 22 towards the radiation detector 18 and the collimator 20 may be an additional/second collimator that restricts the radiation rays 22 from passing into the first imaging region 26. Additionally, the second 28 and the third 30 imaging regions may be spaced apart from the first imaging region 26 so as to reduce the risk that the body part 66, e.g., breast, is exposed to radiation during imaging of the biopsy samples 12, 14.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for imaging biopsy samples obtained from a patient is provided. The system includes: a radiation source operative to emit radiation rays and selectively adjustable between a first scanning position and a second scanning position; a radiation detector operative to receive the radiation rays and having a surface that defines a first imaging region, a second imaging region, and a third imaging region; and a collimator having a body defining an opening and operative to be disposed adjacent to the radiation source such that the collimator is selectively adjustable between a first imaging position and a second imaging position. The first imaging position allows one or more of the radiation rays to pass from the radiation source, through the opening, and into the second imaging region while restricting the radiation rays via the body from passing into the first imaging region when the radiation source is in the first scanning position. The second imaging position allows one or more of the radiation rays to pass from the radiation source, through the opening, and into the third imaging region while restricting the radiation rays via the body from passing into the first imaging region when the radiation source is in the second scanning position. In certain embodiments, the radiation rays are x-rays. In certain embodiments, the body of the collimator has a static shape. In certain embodiments, the collimator is mounted to one or more face shield rails disposed on the radiation source. In certain embodiments, the collimator is adjusted between the first and the second imaging positions by at least one of rotating and translating the body. In certain embodiments, the opening defined by the body of the collimator is disposed along an outer edge of the body. In certain embodiments, the body has a rectangular shape and the opening is defined by a cut-away corner of the body. In certain embodiments, a longitudinal axis of the radiation source forms a positive angle and a negative angle with a line normal to the surface of the radiation detector when the radiation source is in the first and in the second scanning positions, respectively. In certain embodiments, the system further includes a compression plate that compresses a body part of the patient against the surface of the radiation detector within the first imaging region. In such embodiments, the system further includes a biopsy tool operative to obtain the plurality of biopsy samples from the body part of the patient.

Other embodiments provide for a method for imaging a biopsy sample obtained from a patient. The method includes: imaging a body part of the patient disposed in a first imaging region via a radiation source arranged in a first scanning position, the first imaging region defined by a surface of a radiation detector that receives radiation rays emitted by the radiation source and further defines a second imaging region and a third imaging region; obtaining the biopsy sample from the body part; and imaging the biopsy sample in the second imaging region via the radiation source arranged in the first scanning position with a collimator disposed adjacent to the radiation source and arranged in a first imaging position such that an opening defined by a body of the collimator allows one or more of the radiation rays emitted by the radiation source to pass into the second imaging region while the body restricts the radiation rays from passing into the first imaging region. The collimator is selectively adjustable to a second imaging position that allows one or more of the radiation rays emitted by the radiation source to pass through the opening and into the third imaging region while restricting the radiation rays via the body from passing into the first imaging region when the radiation source is arranged in a second scanning position. In certain embodiments, the radiation rays are x-rays. In certain embodiments, the body of the collimator has a static shape. In certain embodiments, the collimator is mounted to one or more face shield rails disposed on the radiation source. In certain embodiments, the method further includes selectively adjusting the collimator from the first to the second imaging position by at least one of rotating and translating the body. In certain embodiments, the body has a rectangular shape and the opening is defined by a cut-away corner of the body. In certain embodiments, a longitudinal axis of the radiation source forms a positive angle and a negative angle with a line normal to the surface of the radiation detector when the radiation source is arranged in the first scanning position and in the second scanning position, respectively. In certain embodiments, the method further includes: compressing the body part against the surface of the radiation detector via a compression plate prior to imaging of the body part via the radiation source arranged in the first scanning position; obtaining, after imaging the biopsy sample in the second imaging region, a subsequent biopsy sample from the body part; and imaging the subsequent biopsy sample in the second imaging region via the radiation source arranged in the first scanning position with the collimator arranged in the first imaging position. In such embodiments, the body part remains compressed via the compression plate until after imaging of the subsequent biopsy sample in the second imaging region.

Yet still other embodiments provide for a collimator for a system for imaging biopsy samples obtained from a patient. The collimator includes a body that defines an opening and is operative to be disposed adjacent to a radiation source of the system. When the body is in a first imaging position and the radiation source is in a first scanning position, the opening allows radiation rays emitted by the radiation source to pass through and into a first imaging region defined by a surface of a radiation detector of the system while restricting the radiation rays from passing into a second imaging region defined by the surface of the radiation detector. When the body is in a second imaging position and the radiation source is in a second scanning position, the opening allows radiation rays emitted by the radiation source to pass through and into a third imaging region defined by the surface of the radiation detector while restricting the radiation rays from passing into the second imaging region. In certain embodiments, the collimator is selectively adjustable between the first and the second imaging positions by at least one of rotating and translating the body. In certain embodiments, the body has a rectangular shape and the opening is defined by a cut-away-corner of the body.

Accordingly, as will be appreciated, by utilizing a collimator to allow the radiation rays emitted by the radiation source to pass into either the second or third imaging regions while shielding the body part, e.g., the patient's breast, in the first imaging region, some embodiments of the invention allow for multiple biopsy samples to be imaged via the same x-ray system, i.e., the radiation source and radian detector, that is utilized to provide the x-ray imagery for guiding the biopsy tool for obtaining the biopsy samples while limiting the patient's exposure to the radiation rays. Accordingly, some embodiments of the invention provide for faster biopsy procedures which reduce the amount of time that the patient's body part must remain compressed. Thus, some embodiments reduce the discomfort often associated with many biopsy procedures.

Further, by utilizing the same x-ray system, i.e., the radiation source and the radiation detector, to both provide the imagery for guiding the biopsy tool and for imaging the biopsy samples, some embodiments of the invention may reduce the number of x-ray imaging systems required for a biopsy procedure and/or provide for the centralized storage of the x-ray image data associate with both guiding the biopsy tool and imaging the biopsy samples.

Further still, by utilizing a collimator that can be selectively adjusted between a first and a second imaging positions via rotating and/or translating the body of the collimator, some embodiments of the invention provide for the ability to image biopsy samples with the same x-ray system used for guiding the biopsy tool without the need to modify the x-ray system so as to provide additional degrees of freedom ("DOF") in the movement of the support structure.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for imaging biopsy samples obtained from a patient comprising:
   a radiation source operative to emit radiation rays and selectively adjustable between a first scanning position and a second scanning position;
   a radiation detector operative to receive the radiation rays and having a surface that defines a first imaging region, a second imaging region, and a third imaging region;
   a collimator having a body defining an opening and operative to be disposed adjacent to the radiation source such that the collimator is selectively adjustable between a first imaging position and a second imaging position; and
   wherein a size and a shape of the opening remains constant whether in the first imaging position or the second imaging position;
   wherein the first imaging position allows one or more of the radiation rays to pass from the radiation source, through the opening, and into the second imaging region while restricting the radiation rays via the body from passing into the first imaging region when the radiation source is in the first scanning position,
   wherein the second imaging position allows one or more of the radiation rays to pass from the radiation source, through the opening, and into the third imaging region while restricting the radiation rays via the body from passing into the first imaging region when the radiation source is in the second scanning position; and
   wherein the collimator is operative to be moved to allow one or more of the radiation rays to pass from the radiation source into the first imaging region when the radiation source is in the first scanning position, and one or more of the radiation rays to pass from the radiation source into the first imaging region when the radiation source is in the second scanning position.

2. The system of claim 1, wherein the radiation rays are x-rays.

3. The system of claim 1, wherein the body of the collimator has a static shape.

4. The system of claim 1, wherein the collimator is mounted to one or more face shield rails disposed on the radiation source.

5. The system of claim 1, wherein the collimator is adjusted between the first and the second imaging positions by at least one of rotating and translating the body.

6. The system of claim 1, wherein the body has a rectangular shape and the opening is defined by a cut-away corner of the body.

7. The system of claim 1, wherein a longitudinal axis of the radiation source forms a positive angle and a negative angle with a line normal to the surface of the radiation detector when the radiation source is in the first and in the second scanning positions, respectively.

8. The system of claim 1 further comprising:
- a compression plate that compresses a body part of the patient against the surface of the radiation detector within the first imaging region; and
- a biopsy tool operative to obtain the plurality of biopsy samples from the body part of the patient.

9. The system of claim 1, wherein:
- the opening is disposed on the outer edge of the body such that at least a portion of the opening is not bounded by the body.

* * * * *